(12) United States Patent
Parratt et al.

(10) Patent No.: US 6,333,418 B1
(45) Date of Patent: Dec. 25, 2001

(54) CYCLISATION PROCESS

(75) Inventors: Julian Simon Parratt, Holyhead; Stephen John Clifford Taylor, Isleham, both of (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/380,293

(22) PCT Filed: Jul. 13, 1999

(86) PCT No.: PCT/SE99/01268
  § 371 Date: Aug. 31, 1999
  § 102(e) Date: Aug. 31, 1999

(87) PCT Pub. No.: WO00/03982
  PCT Pub. Date: Jan. 27, 2000

(30) Foreign Application Priority Data

Jul. 17, 1998 (GB) .................................... 9815552

(51) Int. Cl.$^7$ ................................................ C07D 205/08
(52) U.S. Cl. ............................................................ 548/953
(58) Field of Search ............................................. 548/953

(56) References Cited

U.S. PATENT DOCUMENTS

| 4,870,189 | 9/1989 | Lo et al. ............................. 548/954 |
| 4,946,839 | 8/1990 | Kozikowskip et al. ............. 514/210 |
| 6,150,536 | 11/2000 | Chondroudis et al. ............ 549/2 |

FOREIGN PATENT DOCUMENTS 0 109 411 A1  11/1980 (EP) .
924589  4/1963 (GB) .

OTHER PUBLICATIONS

Fowden, Dr. L., "Azetidine–2–Carboxylic Acid . . . ," Nature, vol. 176, No. 4477, pp. 347–349 (1955).
Emmer, G., "Synthesis of (2RS,E)–3–Ethylidene . . . ," Tetrahedron, vol. 48, No. 35, pp. 7165–7172 (1992).
Eliel et al, "Sterochemistry of Organic Compounds".
Streitwiesser, Jr., "Introduction to Organic Chemistry," 2d Ed.
Fowden, L., "Azetidine–2–carboxylic Acid . . . ," vol. 64, pp. 323–333 (1956).
Yamada et al, "The Synthesis of . . . ," Agr. Biol. Chem., vol. 37, No. 3, pp. 649–652 (1973).
Pichat et al, No. 641—"Synthesis de l'acide . . . ," Bulletin de la Societe Chimique de France, No. 10, pp. 4079–4081 *1968.
Hamilton, P., "Proline: Synthesis from Ornithine . . . ," pp. 587–597 (1952).
Vergruggen et al, "Synthesis of the proline . . . ," FEBS Letters, vol. 308, No. 3, pp. 261–263 (1992).
Rodebaugh et al., "A Facile New Synthesis of . . . ," Communication to the Editor, Jun. 1969, pp. 435–437.
Verbruggen et al, "Synthesis of the proline analogue . . . ," FEBS letters, vol. 308, No. 3, pp. 261–263 (1992).
Chemical Abstracts No. 120734r "Optically active azetidine–carboxylic acid," 27 Heterocycles, vol. 80, p. 419 (1974).

*Primary Examiner*—Bruck Kifle
(74) *Attorney, Agent, or Firm*—Nixon & Vanderhye

(57) ABSTRACT

There is provided a process for the cyclisation of 4-amino-2-halobutyric acid to azetidine-2-carboxylic acid wherein more than 20 g of 4-amino-2-halobutyric acid is cyclised per liter of reaction mixture.

9 Claims, No Drawings

CYCLISATION PROCESS

FIELD OF THE INVENTION

This invention relates to an extremely highly volume efficient process for the production of racemic azetidine-2-carboxylic acid.

BACKGROUND TO THE INVENTION

Azetidine-2-carboxylic acid is an unusual amino acid, the (S)-enantiomer of which is known to be useful in the synthesis of inter alia high molecular weight polypeptides and in particular as an analogue of the well known amino acid proline.

This amino acid is of limited availability from natural sources and consequently the development of an efficient and economic synthetic method for its production is desirable.

That 4-amino-2-halobutyric acids may be cyclised under basic conditions to form azetidine-2-carboxylic acid has been known for many years. For example, Fowden (in Biochem. J. (1956) 64, 323) employed barium hydroxide and Duplan et al (in Bull. Soc. Chem. Chim. France (1968) 4079) employed sodium hydroxide to effect the conversion.

The person skilled in the art would anticipate that in order to maximise the efficiency of intermolecular cyclisation to form the strained four-membered ring, the reaction should be carried out at low concentrations. At higher concentrations it would be expected that the prevalence of competing reactions, such as intramolecular displacement of the bromine atom to form dimers, oligomers or polymers, would significantly decrease efficiency. Indeed, the above authors report only low concentrations (e.g. 10 to 15 g/L) of halo- (in this case bromo-) amino acid; the use of higher concentrations is not suggested.

It will also be appreciated by those skilled in the art that concentrations of the magnitude reported in the above-mentioned prior art are of little practical utility in large scale industrial synthesis. Typical problems which are encountered include poor vessel utilisation, higher effluent output and increased difficulty in product isolation, all of which can render a process economically unviable.

Surprisingly, we have found that the aforementioned cyclisation may be carried out cleanly and efficiently at concentrations which are high enough to be of practical utility in an industrial process.

DESCRIPTION OF THE INVENTION

According to the invention there is provided a process for the cyclisation of 4-amino-2-halobutyric acid to azetidine-2-carboxylic acid wherein more than 20 g of 4-amino-2-halobutyric acid is cyclised per liter of reaction mixture (hereinafter referred to as "the process according to the invention").

In particular, we have found that a highly volume efficient cyclisation may be achieved by adding the 4-amino-2-halobutyric acid as its hydrohalide salt to hot aqueous base (e.g. sodium hydroxide).

Preferred haloamino acids include the chloroamino acid.

Although, in the process according to the invention, more than 20 g of 4-amino-2-halobutyric acid is cyclised per liter of reaction mixture, we have found that significantly higher amounts substrate per liter of reaction mixture may be cyclised with ease. In view of this, and the aforementioned problems associated with lower concentrations, we prefer that, in the process according to the invention, more than 30, more preferably more than 50, especially more than 75 and particularly more than 100 g of substrate is cyclised per liter of reaction mixture.

The product may be isolated in accordance with techniques which are well known to those skilled in the art.

However, we have found that the in situ benzoylation of azetidine-2-carboxylic acid using benzoyl chloride (Schotten Baumann reaction), followed by extraction of the N-benzoyl derivative, provides for efficient product isolation. When such a technique is employed in conjunction with the process according to the invention we have advantageously found that the high concentrations of azetidine-2-carboxylic acid formed facilitates the formation, and isolation, of its N-benzoyl derivative, and avoids excessive unproductive formation of benzoic acid which tends to compete at lower concentrations.

The process according to the invention may for example be carried out by adding small amounts of haloamino acid hydrohalide salt, dissolved in water, dropwise to a solution of base (e.g. sodium hydroxide) at high temperature, for example above 80° C. (e.g. 100–105° C.). We have found that such a technique keeps the transient substrate concentration low, thus reducing the rate of any competing intermolecular reaction.

The process according to the invention has the advantage that the overall reaction volume is kept to a minimum level which makes for a more viable industrial process.

EXAMPLE

Preparation of N-benzoylazetidine-2-carboxylic acid

Sodium hydroxide (277 g, 6.93 mol) was dissolved in water (2.25 L) and the solution heated to 105° C. with efficient over-head stirring. A solution of 4-amino-2-chlorobutyric acid hydrochloride (366 g, 2.10 mol) in water (500 ml) was added over 20 minutes, maintaining a reaction temperature of above 100° C. Upon complete addition, the reaction was stirred for a further five minutes at 100–105° C. and then allowed to cool to 45° C. (approximately four hours). The pH was adjusted to 8.5 with concentrated hydrochloric acid and the solution cooled on an ice-water bath until an internal temperature of 4° C. was attained. Benzoyl chloride (244 ml, 2.10 mol) was added over 30 minutes maintaining a reaction temperature of <8° C. and pH 8.5 (titrating with 10N NaOH). Upon complete addition of benzoyl chloride, the reaction was stirred for a further fifteen minutes (when a total base uptake of 4.2 mol had occurred). The pH was adjusted to 9.5 (c. NaOH) and dichloromethane (1 L) added with efficient stirring. The organic layer was separated and the aqueous phase extracted again with dichloromethane (1 L). The aqueous solution was acidified to pH 1.5 with concentrated hydrochloric acid and extracted with dichlorometane (3×1 L). These combined organic solutions were washed with brine (500 ml), dried ($MgSO_4$), filtered and evaporated in vacuo to yield a pale yellow solid (152 g). $^1H$ NMR spectroscopy ($CDCl_3$, 200 MHz) was consistent with its structure as being the required compound, N-benzoyl-2-azetidinecarboxylic acid.

What is claimed is:

1. A process for the cyclisation of 4-amino-2-halobutyric acid to azetidine-2-carboxylic acid wherein more than 30 g of 4-amino-2-halobutyric acid is cyclised per liter of reaction mixture.

2. A process as claimed in claim 1, characterised in that more than 50 g/L of 4-amino-2-halobutyric acid is cyclised.

3. A process as claimed in claim 2, characterised in that more than 100 g/L of 4-amino-2-halobutyric acid is cyclised.

4. A process as claimed in claim 1, characterised in that the 4-amino-2-halobutyric acid is 4-amino-2-chlorobutyric acid.

5. A process as claimed in claim 1, characterised in that the 4-amino-2-halobutyric acid is added as its hydrohalide salt to hot aqueous base.

6. A process as claimed in claim 5, characterised in that the base is sodium hydroxide.

7. A process as claimed in claim 5, characterised in that the base is at a temperature of more than 80° C.

8. A process as claimed in claim 1, characterised in that haloamino acid hydrochloride salt, dissolved in water, is added dropwise to a solution of base.

9. A process as claimed in claim 1 wherein the azetidine-2-carboxylic acid is subsequently benzoylated in situ using benzoyl chloride and the N-benzoyl derivative is extracted.

* * * * *